United States Patent [19]

Demmer et al.

[11] Patent Number: 4,861,786

[45] Date of Patent: Aug. 29, 1989

[54] COMPOSITION FOR A STABLE VEIN COMPATIBLE INJECTABLE SOLUTION OF TORASEMIDE PROCESS FOR THE PREPARATION AND METHOD OF USE

[75] Inventors: Fritz Demmer, Hirschberg-Leutershausen; Werner Gruber, Birkenau; Heinrich Woog, Laudenbach, all of Fed. Rep. of Germany

[73] Assignee: Boehringer Mannheim GmbH, Mannheim, Fed. Rep. of Germany

[21] Appl. No.: 71,201

[22] Filed: Jul. 8, 1987

[30] Foreign Application Priority Data

Jul. 12, 1986 [DE] Fed. Rep. of Germany ....... 3623620

[51] Int. Cl.$^4$ .............................................. A61K 31/64
[52] U.S. Cl. ..................... 514/347; 514/345; 514/346; 514/869
[58] Field of Search ................. 514/345, 346, 347, 869

[56] References Cited

U.S. PATENT DOCUMENTS

| | | | |
|---|---|---|---|
| 4,020,162 | 4/1977 | Ghilardi et al. | 424/227 |
| 4,301,160 | 11/1981 | Leeb et al. | 424/241 |
| 4,711,906 | 12/1987 | Vonstetten | 514/561 |
| 4,743,693 | 5/1988 | Topfmeier et al. | 546/291 |

FOREIGN PATENT DOCUMENTS 0030681 6/1981 Fed. Rep. of Germany.
3241765 5/1984 Fed. Rep. of Germany.
0185374 6/1986 Fed. Rep. of Germany.
2261011 9/1975 France.

OTHER PUBLICATIONS

Arzneimittel Forschung/Drug Research, Band 35 (II) Oct. 1985.
Remington's Pharmaceutical Sciences, Chapter 84, 1980 1466-1468, pp. 1532-1535.

Primary Examiner—William R. Dixon, Jr.
Assistant Examiner—Jerry D. Johnson
Attorney, Agent, or Firm—Felfe & Lynch

[57] ABSTRACT

The present invention provides an aqueous, alkaline injection solution of torasemide ready for injection, which contains a physiologically compatible alkaline buffer with a pH value of from 9.3 to 9.9 and with a buffer capacity of up to 0.1 val/liter together with an organic solvent in an amount of from 5 to 20% by weight selected from the group of polyethylene glycols with a molecular weight of from 100 to 1500, polypropylene glycols with a molecular weight of from 50 to 1000, glycerol, propylene glycol, ethanol and propanol, the torasemide being present in a concentration of from 2 to 40 mg/ml. Torasemide solutions are useful to inhibit inflammation or promote diuresis.

The present invention also provides a process for the preparation of this solution, wherein torasemide is suspended in the above organic solvent brought into solution by the addition of aqueous alkali, adding the buffer and other adjuvants and adjusting the PH value to 9.3 to 9.9.

19 Claims, No Drawings

COMPOSITION FOR A STABLE VEIN COMPATIBLE INJECTABLE SOLUTION OF TORASEMIDE PROCESS FOR THE PREPARATION AND METHOD OF USE

The present invention is concerned with new, aqueous alkaline injection solutions of torasemide which are ready to inject, are stable and are vein compatible, as well as with processes for the preparation thereof.

Pyridine derivatives with inflammation-inhibiting and diuresis-promoting properties are known from Federal Republic of Germany Patent Specification No. 25 16 025. According to this Patent Specification, these compounds are to be administered as dragees, tablets, capsules or suppositories in dosages of from 50 to 300 mg. of active substance. The most interesting compound of this group has, in the meantime, been recognised to be 1-isopropyl-3[(4-m-toluidino-3-pyridyl)-sulphonyl]-urea, which possesses outstanding diuretic properties. This compound has now been given the generic name of "toasemide".

Although prolonged medication with such compounds usually takes place in the form of solid preparations, it is desirable, especially for clinical use, also to have available an injectable form of composition. In order not, in the case of the use thereof, to have to mix the components with one another, such a solution should be ready to inject, i.e. should contain all the necessary components in the correct mixing ratio in one ampoule. Surprisingly, attempts to prepared torasemide in conventional injectable compositions were unsuccessful. Such compositions are either not vein-compatible or not sufficiently stable so that, especially in the case of prolonged storage, the solution recrystallise or decomposition products separate out which excludes a use for injection purposes.

Therefore, the task exists of finding a formulation with which torasemide can be brought into a compatible, storage-stable, injectable solution in the necessary concentration of 2 to 40 mg./ml.

The solubility in water of torasemide in the form of the sodium or potassum salt is about 250 mg./ml., a pH value of about 9.5 thereby being obtained since torasemide is a relatively weak acid. This solubility should, in itself, be completely sufficient in order to produce injection solutions which only have to contain about 2 to 40 mg/ml.

However, as stated hereinbefore, upon standing, cyrstals separate out from such solutions so that they are not suitable as injection solutions ready for injection. An increase of the pH value of the solution to a value of above 10 admittedly prevents a crystallising out of the torasemide but results in a vein incompatibility of the solution. Furthermore, after some time, sparingly soluble decomposition products are formed which, in turn, precipitate out and must be removed before using the solutions. In addition. the solution slowly loses its content of active material. Consequently, the solution becomes totally useless for injection purposes.

Surprisingly, however, stable, particle-free, vein-compatible injection solutions are obtained when there are added to the solution, on the one hand, a physiologically compatible alkaline buffer with a pH value of from 9.3 to 9.9 and, on the other hand, an organic solvent selected from the group polyethylene glycol, polypropylene glycol, glycerol, propylene glycol, ethanol and propanol.

Thus, according to the present invention, there is provided an aqueous, alkaline injection solution of torasemide ready for injection, wherein it contains a physiologically compatible alkaline buffer with a pH value of from 9.3 to 9.9 and with a buffer capacity of up to 0.1 val/liter and an organic solvent in an amount of from 5 to 20% by weight selected from the group polyethylene glycols with a molecular weight of from 100 to 1500, polypropylene glycols with a molecular weight of from 50 to 1000, glycerol, propylene glycol, ethanol and propanol, the torasemide being present in a concentration of from 2 to 40 mg./ml.

A sufficient vein-compatibility is ensured when the buffer capacity is kept below 0.1 val/liter and the amount of solvent is kept in the range of from 5 to 20% by weight. The amounts of active material and of additives are to be such that, if possible, isotonic solutions are obtained. Insofar as this is not already ensured by the above-mentioned components, in addition there can also be added other materials conventionally used for this purpose, such as sodium chloride, fructose, lactose, glucose and the like, for the adjustment of the isotonic state.

As solvents, there are preferred polyethylene glycols with a molecular weight of from 100 to 1500, especially with a molecular weight of from 200 to 600 and more especially with a molecular weight of about 400. However, the other above-mentioned solvents can also be used although, in these cases, after comparatively long storage, a slight particle formation is to be observed. The solvent should usually be added in an amount of from about 5 to 20% by weight, an addition of about 10% by weight being preferred.

According to the present invention, we have also found that it is important to free the solvents, before their use, from substantially all aldehydes and ketones, an aldehyde content of less than 30 ppm and preferably of less than 10 ppm thereby being maintained. In the case of the use of otherwise conventional solvents with an aldehyde content which is not precisely defined, we have found that torasemide, in the case of comparatively long storgae in solution, partly decomposes into various compounds and that these decomposition products, in turn, react with the aldehydes or ketones present in the solution to give especially sparingly soluble compounds which precipitate out from the solution as small particles. In order to prevent this process, those solvents are preferably used, the aldehyde content of which lies within the above-mentioned limits. The injectable solution of torasemide should have a maximum total aldehyde content of 30 ppm. The term "aldehyde" means not only formaldehyde but also the higher homologous aldehydes which can be formed by oxidation or decomposition of the particular alcohols used as organic solvents.

A purification of the solvent in question usually takes place by appropriate distillation but an addition of appropriate reducing agents, for example metal hydrides or metals, such as lithium, sodium or potassium, is also possible since the alkali metal hydroxide thereby formed can subsequently serve for dissolving the torasemide.

In order to avoid a subsequent formation of such aldehydes or ketones, the injection solutions are produced and stored in an oxygen-free atmosphere, for example under nitrogen. The addition of small amounts of physiologically compatible reducing agents, for example ascorbic acid, can also be useful for this purpose.

As physiologically compatible buffers, it is especially preferred to use the sodium, potassium or ammonium salts of weak acids, for example carbonates, phosphates, glycinates or arginates, N-methylglucosaminate or other amino acids, but there can also be advantageously used, for example, the readily compatible tris-(hydroxymethyl)-aminomethane (trometamol). A special case of buffering can also consist in the addition of a further active material acting as buffer, for example, in the addition of canrenoate or furosemide sodium or potassium salts. Since the torasemide is present in the injection solution in an amount of about 0.01 to 0.2 mole/liter, an amount of buffer of from 0.01 to 0.1 val/liter has proved to be especially favourable. This range combines a sufficient buffering with a good vein compatibility which, especially in the case of high buffer concentrations, is no longer obtained.

The preparation of the injection solutions according to the present invention preferably takes place by suspending the active material in the organic solvent used with a part of the water required and brought into solution by the addition of aqueous alkali or ammonia. Thereafter, the buffer and other adjuvants are added thereto and the desired pH value of from 9.3 to 9.9 is adjusted by the addition of small amounts of acids or alkalis.

Alternatively, the torasemide salt itself can, of course, also be used.

The torasemide used preferably has a particle size of less than 10 μm. and more preferably of less than 2 μm.

The solution thus obtained is filtered free of particles possible present and sterilised. for sterilisation, heating to 100° to 130° C. has proved to be especially useful since this less laborious than a sterile filtration. Before the heat sterilisation, the solution is usually filled into ampoules, ampoule sizes of 5 to 20 ml. with active materials contents of from 10 to 200 mg. of active materials per ampoule having proved to be useful. The ampoules are usually filled under nitrogen and, at ambient temperature, prove to be storage-stable for at least 3 years without turbidity appearing or without the active materials being chemically changed to any significant extent.

Because of the small buffer capacity, the solutions do not give rise to significant pH value changes at the point of injection so that an undiluted administration is possible. However, the solutions according to the invention can also be mixed with an isotonic glucose or sodium chloride solution and then administered.

For the preparation of isotonic and/or injectable solutions, it is, of course, also possible first to prepare solutions which have a buffer capacity greater than 0.1 val/liter and then to bring these, by the addition of an appropriate acid, for example hydrochloric acid, to a pH value of 7.0 to 7.5 but preferably to the pH value of blood of 7.4, the isotonic injection solution ready for injection thereby being obtained simultaneously by the dilution carried out.

The injection solutions according to the present invention can, of course, also contain conventional adjuvants and additives which make them suitable for administration, for example tensides, mineral materials, vitamins and the like.

The following Examples are given for the purpose of illustrating the present invention:

EXAMPLE 1

Torasemide 20 mg./4 ml. injection solution

In a sterile 50 liter V2A double-mante kettle provided with a stirrer are placed 30 liters of water for injection purposes and 4.5 kg. polyethylene glycol 400 and 16.0 g. sodium hydroxide are dissolved therein with nitrogen gassing, light protection and stirring. 200 g. micronised torasemide are then suspended therein, while stirring vigorously, and, in part, dissolved. The remaining torasemide is dissolved by adding a solution of 8 g. sodium hydroxide in 200 ml. water for injection purposes and the pH value is adjusted to 9.6 to 9.8, whereafter 5 g. tris-(hydroxymethyl)-aminomethane are added thereto and dissolved with stirring. The batch is made up to an end volume of 40 liters with water for injection purposes and stirred. The solution is sterile filtered over membrane filters of 0.2 μm. pore width and the sterile-filtered solution is filled to 4.2 ml. amounts into 5 ml. ampoules. The ampoules are sterilised in an autoclave at 121° C. for 20 minutes, a clear injection solution ready for injection being obtained which can be stored for at least 3 years without turbidity and decomposition. The pH value of this solution is 9.5 and the titration basicity corresponds to 9.7 ml. 0.1 N hydrochloric acid which is needed per ampoule for lowering the pH value from 9.5 to 7.4.

EXAMPLE 2

Torasemide 200 mg/20 ml. injection solution in the form of torasemide sodium

In a sterile 200 liter V2A double-mantle kettle provided with a stirrer are placed 150 liters of water for injection purposes and 22.5 kg. of polyethylene glycol 400 and 198 g. sodium hydroxide are dissolved therein with nitrogen gassing, light protection and stirring. 2 kg. micronised torasemide are then suspended therein with vigorous stirring and, in part, dissolved. The remaining torasemide is dissolved by adding a solution of 40 g. sodium hydroxide in 1000 ml. water for injection purposes and the pH value is adjusted to 9.6 to 9.8. 15 g. Trisodium phosphate are then added thereto and dissolved with stirring. The batch is made up to the end volume of 200 liters with water for injection purposes, stirred and sterile filtered over a membrane filter with the pore width of 0.2 μm. The sterile-filtered solution is filled in 20.5 ml. amounts into ampoules and sterilised in an autoclave at 121° C. for 20 minutes. A clear injection solution ready for injection is thus obtained which can be stored for at least 3 years without turbidity and decomposition. The pH value of the injection solution is 9.5 and the titration basicity corresponds to 19.4 ml. 0.1N hydrochloric acid which is needed per ampoule for lowering the pH value from 9.5 to 7.4.

EXAMPLE 3

Torasemide 100 mg./10 ml. injection solution in the form of torasemide potassium In a sterile 100 liter V1A double mantle kettle provided with stirrer are placed 75 liters water for injection purposes and 10 liters ethanol and 150 g. potassium hydroxide are dissolved therein with nitrogen gassing, light protection and stirring. 1 kg. micronised torasemide is suspended therein with vigorous stirring and, in part, dissolved. The remaining torasemide in dissolved by adding a solution of 62 g. potassium hydroxide in 500 ml. water for injection purposes and the pH value is adjusted to 9.6 to 9.8. 5 g. Potassium carbonate are added thereto and dissolved with stirring. The batch is made up to an end volume of 100 liters with water for injection purposes, stirred up and sterile filtered over a membrane filter with a pore width of 0.2 μm. The sterile filtered solution is filled in 10.5 ml. amounts into ampoules and sterilised in an autoclave at 121° C. for 20 minutes. A clear injection solution ready for injection is thus obtained which can be stored for at least 3 years without turbidity and decomposition. The pH value of the injection solution is 9.5 and the tritration basicity corresponds to 9.8 ml. 0.1N hydrochloric acid which is needed per ampoule for lowering the pH value from 9.5 to 7.4.

EXAMPE 4

Torasemide 100 mg./10 ml. injection solution in the form of torasemide potassium and arginine as buffer.

In a sterile 100 liter V2A double-mantle kettle provided with stirrer are placed 75 liters water for injection purposes and 150 g. potassium hydroxide are dissolved therein with nitrogen gassing, light protection and stirring. 1 kg. micronised torasemide is suspended therein with vigorous stirring and, in part, dissolved. The remaining torasemide is dissolved by adding a solution of 62 g. potassium hydroxide in 500 ml. water for injection purposes and the pH value is adjusted to 9.6 to 9.8. 5 g. Arginine are added thereto and dissolved with stirring. The batch is stirred up and filtered over a membrane filter with a pore width of 0.2 μm. The filtered solution is filled in 10.5 ml. amounts into ampoules and sterilised in an autoclave at 121° C. for 20 minutes. A clear injection solution ready for injection is obtained which can be stored for at least 3 years without turbidity and decomposition. The pH value of the injection solution is 9.5 and the titration basicity corresponds to 9.8 ml. 0.1N hydrochloric acid which is needed per ampoule for lowering the pH value from 9.5 to 7.4.

EXAMPLE 5

Comparative particle measurements in the case of torasemide injection solutions

Formulations

| composition | 86/1 | 86/2 | 86/3 | 86/4 | 86/5 |
|---|---|---|---|---|---|
| torasemide | 200.0 mg | 200.0 mg | 200.0 mg | 200.0 mg | 200.0 mg |
| trometamol | 1.0 mg | 1.0 mg | 1.0 mg | 1.0 mg | 1.0 mg |
| sodium hydroxide | 23.8 mg | 23.8 mg | 23.8 mg | 23.8 mg | 23.8 mg |
| polyethylene glycol 400 | 2.0 ml | — | — | — | 1.0 ml |
| ethanol | — | 2.0 ml | — | — | 1.0 ml |
| propylene glycol | — | — | 2.0 ml | — | — |
| water for injection ad | 20.0 ml | 20.0 ml | 20.0 ml | 20.0 ml | 20.0 ml |

The particle count was determined according to the British Pharmacopoeia II, 1980, page 578 or U.S. Pharmacopoeia XXI, 1985, 1258. There were measured particles with diameters greater than 2 μm. and particles greater than 25 μm. which, in the following Table, are in each case, given above one another.

Particle measurements

| experiment No. | after 24 h. | after 1 wk. | after 4 wks. | after 8 wks. |
|---|---|---|---|---|
| 86/1 | 164 | 108 | 134 | 67 |
|  | 0 | 0 | 0 | 0 |
| 86/2 | 234 | 287 | 647 | 626 |
|  | 1 | 1 | 1 | 10 |
| 86/3 | 310 | 470 | 682 | 658 |
|  | 2 | 4 | 4 | 43 |
| 86/4 | 444 | 898 | 1297 | 2460 |
|  | 3 | 2 | 23 | 35 |
| 86/5 | 181 | 203 | 390 | 420 |
|  | 0 | 1 | 3 | 7 |

EXAMPLE 6

Combination preparation with 200 mg. furosemide and 10 mg. torasemide/10 ml. injection solution In 6 liters of water for injection purposes are suspended 144.48 g. furosemide and then dissolved by the addition of 5% aqueous potassium hydroxide solution. Thereafter, 8 g. torasemide are suspended in this solution and the pH value is adjusted to 11.0 with 5% aqueous potassium hydroxide solution. There re then added thereto 18.4 g. sodium carbonate and 0.8 liters polyethylene glycol 400 (PEG. 400), as well as 8 liters water for injection purposes. The mixture is vigorously stirred and the pH value again adjusted to 11.0 with aqueous potassium hydroxide solution. The solution is sterile filtered over membrane filters with 0.2 μm. pore width. The sterile-filtered solution is filled in 10.2 ml. amounts into 10 ml. ampoules. The ampoules are sterilised in an autoclave at 121° C. for 20 minutes. A clear injection solution ready for injection is obtained which can be stored for at least 3 years without turbidity or decomposition. The pH value of this solution is from 10.8 to 11.2. The titration basicity corresponds to 5.8 ml. 0.1N hydrochloric acid which are needed per ampoule for lowering the pH value from 11.0 to 7.4.

EXAMPLE 7

Combination preparation with 200 mg. potassium canrenoate and 10 mg. torasemide/10 ml. injection solution 144.48 g. Canrenoic acid are suspended in 6 liters water for injection purposes and dissolved by the addition of 5% aqueous potassium hydroxide solution. Thereafter, 8 g. torasemide are suspended in this solution and the pH value is adjusted to 11.0 with 5% aqueous potassium hydroxide solution. There are then added thereto 18.4 g. sodium carbonate and 0.8 liter polyethylene glycol 400, as well as 8 liters water for injection purposes. The mixture is vigorously stirred and the pH value is again adjusted to 11.0 with aqueous potassium hydroxide solution. The solution is sterile filtered over membrane filters with 0.1 μm. pore width. The sterile-filtered solution is filled in 10.2 ml. amounts in 10 ml. ampoules. The ampoules are sterilised in an autoclave at 121° C. for 20 minutes. A clear solution ready for injection is obtained which can be stored for at least 3 years without turbidity and decomposition. The pH value of this solution is from 10.8 to 11.2. The titration basicity corresponds to 5.8 ml. 0.1N hydrochloric acid which are needed per ampoule for lowering the pH value from 11.0 to 7.4.

EXAMPLE 8

Torasemide 10 mg./2 ml. injection solution

In a sterile 100 liter V2A double-mantle kettle provided with stirrer are placed 50 liters water for injection purposes, 2 kg. polyethylene glycol 400, 1 kg. ethanol and 1.5 kg. propylene glycol and 16.0 g. sodium hydroxide are dissolved therein with nitrogen gassing, light protection and stirring. 200 mg. micronised torasemide are then suspended therein with vigorous stirring and, in part, dissolved. The remaining torasemide is dissolved by adding a solution of 8 g. aqueous sodium hydroxide solution in 200 ml. water for injection purposes and the Ph value is adjusted to 9.6 to 9.8 5 g. Tris-(hydroxymethyl)-aminomethane are added thereto and dissolved with stirring. The batch is made up with water for injection purposes to an end volume of 80 liters and stirred up. The solution is sterile filtered over membrane filters with 0.2 μm. pore width. The sterile filtered solution is filled in 2.2 ml. amounts in 2 ml. ampoules. The ampoules are sterilised at 121° C. for 20 minutes in an autoclave. A clear injection solution ready for injection is obtained which can be stored for at least 3 years without turbidity and decomposition. The pH value of this solution is 9.5 and the titration basicity corresponds to 4.8 ml. 0.1N hydrochloric acid which are needed per ampoule for lowering the pH value from 9.5 to 7.4.

It will be understood that the specification and examples are illustrative but not limitative of the present invention and that other embodiments within the spirit and scope of the invention will suggest themselves to those skilled in the art.

We claim:

1. A composition for an aqueous, sterile, alkaline pharmaceutically active and vein-compatible solution of torasemide for injection in mammals for inhibition of inflammation or promotion of diuresis, comprising 2-40 mg/ml torasemide or a physiologically acceptable salt thereof in a physiologically compatible alkaline buffer of pH 9.3-9.9 and with a buffer capacity of up to 0.1 val/liter, together with an organic solvent substantially free of aldehyde or ketone wherein the organic solvent contains less than 30 ppm aldehyde in an amount of from 5 to 20% by weight selected from the group consisting of at least one of polyethylene glycol in a 100-1500 molecular weight range, polypropylene glycol in a 150-1000 molecular weight range, glycerol, propylene glycol, ethanol and propanol wherein the composition is stored in an oxygen-free atmosphere or in the presence of a physiologically compatible reducing agent.

2. The composition of claim 1 wherein the organic solvent is polyethylene glycol of 200-600 molecular weight.

3. The composition of claim 1 wherein the organic solvent is polyethylene glycol of 400 molecular weight.

4. The composition of claim wherein the organic solvent is about 10% by weight.

5. The composition of claim 1 wherein the torasemide is present in a concentration of 0.01 to 0.2 mole/liter.

6. The composition of claim 1 wherein the torasemide used has a particle size of less than 10 micrometer.

7. The composition of claim 1 wherein the torasamide used has a particle size of less than 2 micrometer.

8. The solution for injection of claim 1, wherein the organic solvent contains less than 10 ppm aldehyde.

9. The torasemide solution for injection of claim wherein the buffer is a sodium, potassium or ammonium salt of a weak acid, a tris-(hydroxymethyl)-aminomethane, or a further physiologically active material acting as a buffer.

10. The torasemide solution of claim 9 wherein the weak acid is a phosphate, carbonate, glycinate, arginate, N-methyl glucosaminate or other amino acid.

11. The torasemide solution of claim 9 wherein the further active material is a diuretic.

12. The torasemide solution of claim 11 wherein the diuretic is canrenoate and/or furosemide.

13. The torasemide solution of claim 9 wherein the further active material is present in an amount of up to 100 mg/ml.

14. The torasemide solution of claim 1 further comprising an agent for the maintenance of the iostonic state.

15. The torasemide solution of claim 14 wherein the agent comprises sodium chloride, fructose, lactose or glucose.

16. The composition of claim 1 further comprising adjuvants and additives from the group of tenside, mineral and vitamin.

17. A kit for the preparation of an injectable solution of torasemide comprising torasemide, a buffer from the group of a sodium, potassium or ammonium salt of a weak acid or tris-(hydroxymethyl)-aminomethane or a further active material acting as an alkaline buffer with a pH of 9.3-9.9, an organic solvent substantially free of aldehyde or ketone wherein the organic solvent contains less than 30 ppm aldehyde selected from the group consisting of at least one polyethylene glycol in a 100-1500 molecular weight range, polypropylene glycol in a 150-1000 molecular weight range, propylene glycol, ethanol and propanol, an agent to maintain isotonicity and a reducing agent.

18. The solution of torasemide for injection of claim 1 prepared by a process of which comprises:
   suspending torasemide in an organic solvent substantially free of aldehyde and ketone wherein the solvent is from the group of polyethylene glycol, polypropylene glycol, glycerol, propylene glycol, ethanol and propanol;
   bringing the torasemide into solution by the addition of an aqueous alkali to a pH value adjusted to 9.3 to 9.9 by the addition of acid or alkali;
   filtering off undissolved particles from the solution, and sterilizing the solution.

19. A method for inhibiting inflammation and promoting diuresis in mammals which comprises injecting the solution of torasemide of claim 1 in a pharmaceutically active amount of mammals in need of such treatment.

* * * * *

UNITED STATES PATENT AND TRADEMARK OFFICE
CERTIFICATE OF CORRECTION

PATENT NO. : 4,861,786
DATED : August 29, 1989
INVENTOR(S) : Fritz Demmer, et al.

It is certified that error appears in the above-identified patent and that said Letters Patent is hereby corrected as shown below:

| | |
|---|---|
| Column 1, line 22 | after "name of", delete "toasemide" and insert -- torasemide --. |
| Column 2, line 42 | after "long", delete "storgae" and insert -- storage --. |
| Column 3, line 34 | after "sterilised.", delete "for" and insert -- For --. |
| Column 4, line 4 | after "double-", delete "mante" and insert -- mantle --. |
| Column 6, line 26 | after "solution.", delete "There re" and insert -- There are --. |
| Column 6, line 59 | after "with" delete "0.1" and insert -- 0.2 --. |
| Column 7, line 62 | after "claim", insert -- 1 --. |
| Column 8, line 9 | after "claim", insert -- 1--. |

UNITED STATES PATENT AND TRADEMARK OFFICE
CERTIFICATE OF CORRECTION

PATENT NO. : 4,861,786
DATED : August 29, 1989
INVENTOR(S) : Fritz Demmer, et al It is certified that error appears in the above-identified patent and that said Letters Patent is hereby corrected as shown below:

Abstract,
last line          delete "PH" and insert --pH--.

Signed and Sealed this

Sixth Day of November, 1990

Attest:

HARRY F. MANBECK, JR.

*Attesting Officer*       *Commissioner of Patents and Trademarks*